United States Patent [19]

Carignan et al.

[11] Patent Number: 4,493,220
[45] Date of Patent: Jan. 15, 1985

[54] FORCE MEASURING PLATFORM AND LOAD CELL THEREFOR USING STRAIN GAGES TO MEASURE SHEAR FORCES

[75] Inventors: Forest J. Carignan, Bedford; Nathan H. Cook, Cambridge, both of Mass.

[73] Assignee: Advanced Mechanical Technology, Inc., Newton, Mass.

[21] Appl. No.: 443,939

[22] Filed: Nov. 23, 1982

[51] Int. Cl.³ .......................... G01L 1/18; G01L 5/16
[52] U.S. Cl. .............................. 73/862.66; 73/862.04
[58] Field of Search ........... 73/862.04, 862.05, 862.06, 73/862.66, 862.67, 767; 128/782

[56] References Cited

U.S. PATENT DOCUMENTS

| | | | |
|---|---|---|---|
| 3,535,923 | 10/1970 | Martorana et al. | 73/141 |
| 3,587,761 | 6/1971 | Merriam et al. | 177/134 |
| 3,618,376 | 11/1971 | Shull et al. | 73/862.04 |
| 3,640,130 | 2/1972 | Spescha et al. | 73/862.04 |
| 3,771,359 | 11/1973 | Shoberg | 73/862.04 |
| 4,046,005 | 9/1977 | Goroski | 73/862.05 |
| 4,094,192 | 6/1978 | Watson et al. | 73/862.04 |
| 4,398,429 | 8/1983 | Cook et al. | 73/862.04 |

FOREIGN PATENT DOCUMENTS 2917967 11/1980 Fed. Rep. of Germany .
757211 9/1956 United Kingdom .

OTHER PUBLICATIONS

Smith et al., "A Six Component Dynanometer", Journal Mechanical Engineering Science, vol. 12, No. 2, Apr. 1970, pp. 143-145.
Cook, Nathan H. and Ernest Rabinowicz, "Physical Measurement and Analysis", Addison-Wesley series in the Engineering Sciences, 1963, pp. 158-167.
Payne, A. H., "A Force Platform System for Biomechanics Research in Sport", Biomechanics, IV, R. C. Nelson, C. A. Morehous, Eds. 1974, pp. 502-507.
Cunningham, Don M., G. Wayne Brown, "Two Devices for Measuring the Forces Acting on the Human Body During Walking", Proc. of the Soc. for Experimental Stress Analysis, vol. IX, No. 2, pp. 75-90.
Watson, P. C. and S. H. Drake, "Pedestal and Wrist Force Sensors for Automatic Assembly", Report for Charles Stark Draper Laboratory, Inc., Cambridge, MA, Jun. 1975.
Patents Abstracts of Japan, vol. 6, No. 212, (P-151) (1090), Oct. 26, 1982, (Tokyo, Japan), 57-118132 (Nitsushiyou Denki K.K.), Jul. 22, 1982.
Ploytechnisch Tijdschrift, Vakgedeelte A, vol. 14, No. 29/30, Jul. 15, 1959, A. Kleepe: "Elektronische meetapparatuur voor de werkplaats, II".

Primary Examiner—Charles A. Ruehl
Attorney, Agent, or Firm—Hamilton, Brook, Smith and Reynolds

[57] ABSTRACT

In a force measuring platform, a top plate 12 is supported on tubular load cells 16. The load cells have strain gages to measure the strain due to the horizontal shear forces. The "shear" strain gages also measure moments about the Z axis when properly placed in a bridge circuit. Strain gages mounted to measure vertical strain indicate vertical forces and moments about horizontal axes.

8 Claims, 9 Drawing Figures

FORCE MEASURING PLATFORM AND LOAD CELL THEREFOR USING STRAIN GAGES TO MEASURE SHEAR FORCES

DESCRIPTION

1. Field of the Invention

This invention relates to dynamometers and in particular to force platforms which measure vertical and horizontal forces and moments using multiple load cells.

2. Background

Measurement of forces by means of a force platform apparatus is well-known in the art. In one desirable form the force platform may be employed in measuring human dynamics and is commonly referred to as a "Biomechanics Platform". The field of application of force platforms including biomechanics platforms has been rapidly widened in recent time and extends into fields of specialized medical application, sports application, running dynamics and the like.

Strain signals induced by forces and torque applied to a platform such as a biomechanics platform are electrically sensed and then transmitted to a receiver to provide a suitable record. Typically, strain gages are placed on rings to which a top plate is mounted. The rings flex with applied force and the strain gages are placed at positions which are strain nodes under certain loads and highly strained under others. It is essential that a high degree of selectivity and accuracy be achieved in the sensing and transmission of strain signals which are related to the forces and moments which produce them. In this connection, difficulty has, in some instances, been experienced due to the fact that erroneous force/moment signals may be sensed and transmitted. Erroneous signals thus sensed are commonly referred to as "cross talk" and may detract materially from the accuracy of measurements obtained.

There are various forms of cross talk and the invention is particularly concerned with one form of cross talk which may be defined as erroneous signals resulting from deformation of a top plate due to applied loads. This type of cross talk may be principally experienced by the horizontal force sensing channels, but may also be experienced in vertical force channels and in moment sensing channels. For example, a purely vertical load on a platform may cause bending of the platform which is sensed by load cells as moments and horizontal forces. Ideally, with a pure vertical load only vertical force is indicated.

The present invention relates in general to force measuring apparatus and in particular to a force platform construction of the class employed in measuring human dynamics and commonly referred to as a "Biomechanics Platform". Such a biomechanics platform, in one desirable embodiment, includes top and bottom plates supported at their corners by load cell structures in which strain rings have strain gages thereon. The load cell structures may deformably support the top plate in spaced relation to the bottom plate.

In our prior, U.S. Pat. No. 4,398,429, we have disclosed a force platform comprising load cell structures which include strain rings having strain gages suitably located thereon. Composite anchoring means are attached between the top plate of the force platform and respective strain rings of each of the load cell structures. Each of the composite anchoring means includes (a) an elastic or compliant member arranged to transmit, at any given time, an entire load exerted between the top plate and individual load cell, and (b) retaining elements for securing a respective resilient or compliant member in predetermined relationship to the top plate and to respective strain ring members. Utilization of compliant or elastic means constructed and arranged as disclosed operates to reduce or eliminate to a very desirable extent transmission of erroneous force signals resulting from deformation of a top plate member and tending to cause cross talk.

Although the load cell of our prior application provides a greatly improved platform with low cross talk, it does have a more complex structure than is usual. Further, the natural frequency of the platform for horizontal vibrations is, in one typical case, to about 140 hertz. The natural frequency must be higher than the frequency of forces being measured; it can thus limit use of the apparatus. Although a frequency of 140 hertz is generally satisfactory, a higher frequency would be an improvement.

DISCLOSURE OF THE INVENTION

In accordance with principles of this invention, horizontal forces are measured by strain gages positioned to measure the strains due to shear rather than those due to bending. When the gages are properly connected in bridge circuits, particular horizontal forces can be isolated with little cross talk. When connected in a Wheatstone bridge, shear gages on a cylindrical load cell can provide zero ouput under vertical loading. The load cell can be a simple column, and vertical forces are measured by gages which measure strains due to compressive loading. To provide for high sensitivity along with stiffness of the load cells, the ideal load cell is tubular.

DESCRIPTION OF A PREFERRED EMBODIMENT

Figure 1:
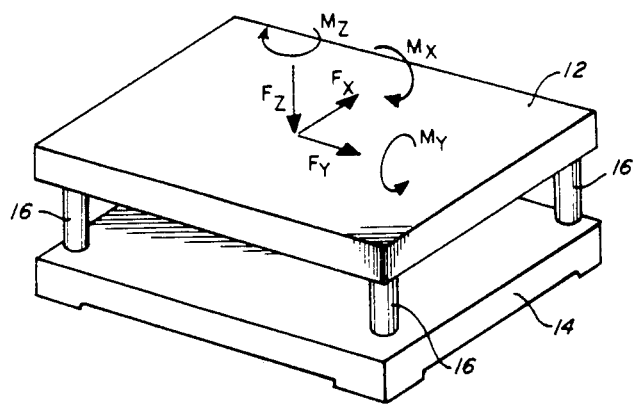
FIG. 1 is a perspective view of a simple force platform comprising load cells in accordance with this invention.

FIG. 1 illustrates generally a force plate construction wherein a top plate 12 and a bottom plate 14 are located in spaced apart relation by load cells 16 arranged at the corners. The forces F and moments M typically measured by the platform are illustrated in FIG. 1.

Figure 2:
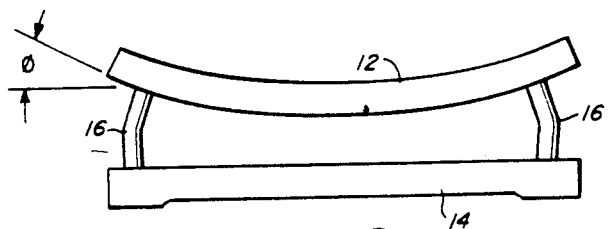
FIG. 2 is a side view of the platform of FIG. 1 with bending of the top plate of the platform exaggerated.
Figure 3:
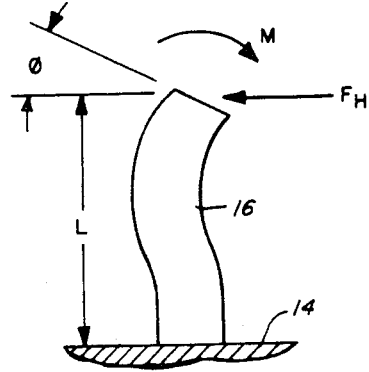
FIG. 3 is an illustration of the moment and horizontal forces applied to a load cell due to bending of the top plate.

FIGS. 2 and 3 diagrammatically illustrate bending of a top plate and suggest how internally generated forces may be transmitted to load cells so that the cells tend to sense forces which are extraneous to the forces applied to the top plate.

As is illustrated in FIG. 2, bending of the top plate causes the top end of a load cell to rotate through an angle $\phi$. There is no significant lateral displacement of the top of a load cell due to bending of the top plate, since it is anchored to the top plate. As illustrated in FIG. 3, under the aforesaid constraints, a bending moment M and a lateral force $F_H$ are applied to the load cell as a result of its rotation through angle $\phi$. The magnitude of the horizontal force, $F_H$, and the moment, M, may be calculated from simple beam theory to be $$F_H = 6EI\phi/L^2; \quad M = 4EI\phi/L$$

where E is Young's modulus of elasticity, I is the moment of inertia of a load cell with respect to its horizontal axis, L is the height of the load cell, and $\phi$ is the angle of rotation of the top of the load cell.

In a typical multiple load cell dynamometer, load cells are rings designed to detect specific loads with specifically placed strain gages. However, in practice, those gages detect forces in addition to those for which they were designed to detect. In accordance with principles of this invention, the top platform 12 is mounted on load cells which are columns having shear gages and vertical compression gages thereon. The shear gages measure horizontal forces, and the vertical compression gages measure vertical forces.

Figure 5:
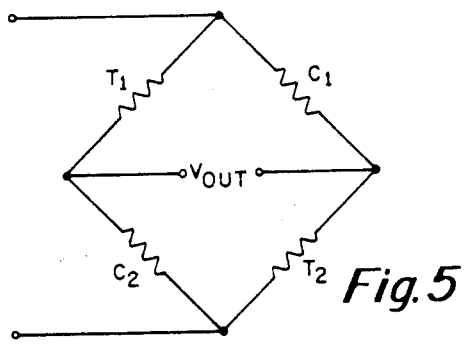
FIG. 5 is an electrical schematic of a Wheatstone bridge in which strain gages are connected.

In a Wheatstone bridge circuit as shown in FIG. 5, equal resistance changes on any adjacent arms of the circuit give zero output. Identical resistance changes on opposite arms of a Wheatstone bridge produce doubled output. Thus for maximum output two opposite arms should undergo one, positive change in resistance while the other two opposite arms should undergo a negative change in resistance.

Figure 4:
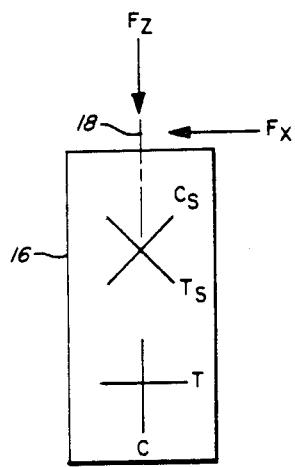
FIG. 4 is a side view of a load cell used in accordance with this invention showing strain gage locations for measuring a horizontal force $F_X$ and a vertical force $F_Z$.

Placement of strain gages according to this invention are illustrated by FIG. 4 which shows several axes of tension and compression on a cylindrical load cell 16. Under the influence of a horizontal force $F_X$ applied to the top of the load cell, the load cell 16 sees a maximum tension due to shear force along an axis $T_S$ and a maximum compression due to shear along the axis $C_S$. These axes are at right angles to each other. When placed in adjacent legs in a Wheatstone bridge as in FIG. 5, the electrical outputs resulting from tension and compression along these axes reinforce each other to provide an output of satisfactory sensitivity. By joining selected gages from plural load cells in respective bridges, each of the forces F and moments M can be isolated.

The horizontal force $F_H$, due to bending of the top plate, produces strain in the shear-force gages. However, because all four load cells are wired to measure the sum of $F_H$ in one direction, and because the forces $F_H$ and opposite load cells are oppositely directed, the net output is zero; the signals are cancelled in the Wheatstone bridge circuit in the usual fashion.

Any positive vertical forces $F_Z$ on the load cell 16 produce equal compressive strains on the axes $T_S$ and $C_S$. With the strain gages placed along these axes positioned in adjacent legs of the bridge, equal strains of the same type, in this case compression, cancel out to provide no change in electrical output from the bridge.

By placing the the shear strain gages along the neutral axis 18 of the load cell 16, any bending of the load cell about the Y axis results in zero average strain in each of the shear gages. As a result, the net resistance of each gage does not change and the bridge provides no change in output. A tubular load cell is particularly suited to assuring that all strain gages are positioned along an appropriate neutral axis of the cell. Any forces in the Y direction into or from the page of FIG. 4 are seen as zero shear. Any moment about the X axis is seen by the shear gages on the outer face of the cylindrical load cell 16 as a vertical force, that is equal compression or tension along each axis.

By placing stacked strain gages in adjacent legs of a bridge, temperature compensation is provided. Any change in resistance of one leg due to temperature changes are also seen by an adjacent leg and the equal changes in resistance of adjacent legs cancel each other in the bridge output.

The sensitivity of a shear strain element is inversely proportional to the cross sectional area of the body under stress. Thus, the cross sectional area of the load cell 16 in a horizontal plane should be held to a minimum. On the other hand, to obtain a stiff load cell which provides a high natural frequency, a thin rod would not be feasible. To provide a small cross sectional area along with stiffness and strength, a tubular load cell is ideal.

Vertical forces are measured by measuring strain along an axis C. That measurement can be reinforced by adding the Poisson strain along the axis T. Poisson strain is a strain which occurs in the direction perpendicular to the primary strain and is of an opposite type. For aluminum, that strain is approximately $-0.32$ times the primary strain. By connecting a Poisson strain gage on an adjacent leg of a Wheatstone bridge, that measured strain reinforces a readout of compressive strain along the axis C.

By placing a stacked rosette gage on the opposite side of the cylindrical load cell, 180 degrees from the axes T and C shown in FIG. 4, any bending of the load cell about the X axis is seen by the vertical gage of one rosette as compression and by the vertical gage of the other stacked rosette as tension. By placing the vertical strain gages which are displaced by 180 degrees on opposite legs of a bridge, those opposite strains cancel each other in the electrical output so that a moment about the X axis is not measured. In compression of the load cell, however, both strain gages along the vertical axes C are in compression, and because the gages are on opposite arms of a bridge, their output is reinforced.

Any moments about the Y or Z axis of FIG. 4 and any horizontal forces will not be seen by the gages on axes T and C. Because the gases are along the neutral axis 18, the net resistances of the gages along the T and C axes do not change with bending about the Y axis.

The applied moments $M_X$ and $M_Y$ are obtained by proper combinations of specific vertical strain measurements in a Wheatstone bridge such that forces not being measured are cancelled. The moment $M_Z$ is measured as a combination of side forces on the several load cells. Side forces other than those resulting from moments are cancelled out in the bridge circuits.

Figure 6:
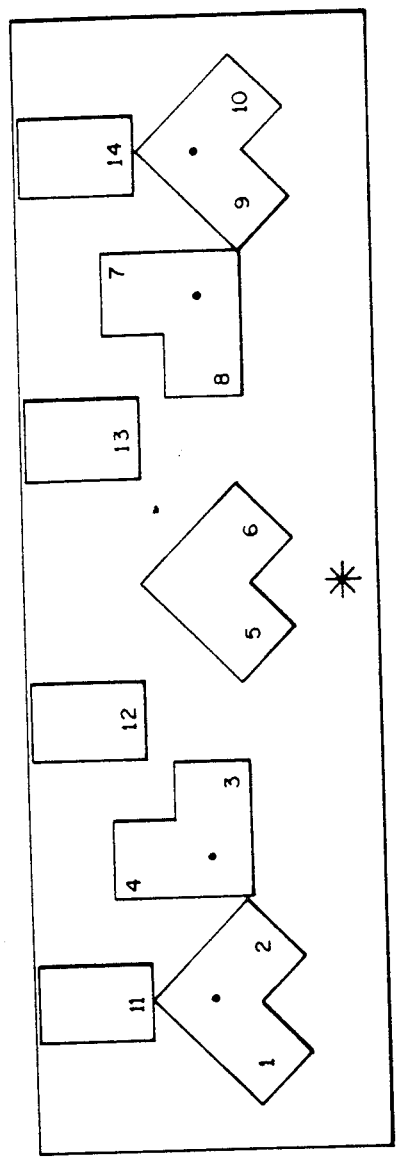
FIG. 6 is a layout of strain gages on an unwrapped cylindrical load cell.
Figure 7:
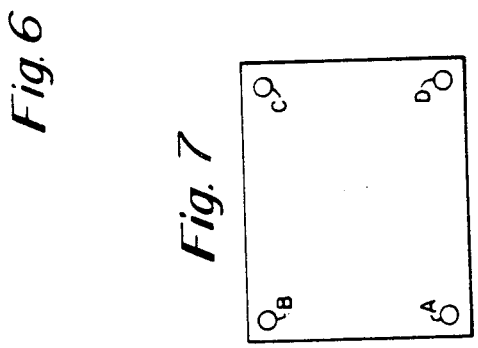
FIG. 7 is a plan view of four load cells in a platform with letter designations.

One arrangement of strain gages on each of four load cells is illustrated by FIG. 6 with reference to FIG. 7. The strain gages are shown on an unwrapped cylindrical load cell as if mounted on tape of a length which matches the circumference of the load cell, which tape can be placed about the cell. The asterisk shown in the layout of FIG. 6 would be positioned toward the bottom of each cell pointing toward the corner of the platform. The gages include three stacked rossettes 1,2; 5,6 and 9,10 for measuring shear strains. Stacked rossettes 3,4 and 7,8 measure vertical compression and tension and Poisson tension and compression. Gauges 11 to 14 measure tension and compression along vertical axes for measuring $M_X$ and $M_Y$. The gages of FIG. 6 are placed on each of the load cells A, B, C and D of FIG. 7.

The strain gages are connected electrically in a Wheatstone bridge of FIG. 5 in order to measure the forces $F_X$, $F_Y$ and $F_Z$ and the moments $M_X$, $M_Y$ and $M_Z$ of FIG. 1. A suitable connection of the gages as elements $T_1$, $T_2$, $C_1$ and $C_2$ of the bridge are illustrated by the following table.

From the table, in the bridge of FIG. 5 which indicates $F_X$, for example, resistance 1 of the bridge is made of two strain elements connected in series. Those elements are gage 1 (FIG. 6) on load cell A (FIG. 7) and gage 2 on load cell C.

TABLE

Gages $T_1$, $T_2$, $C_1$, and $C_2$ In Wheatstone Bridge To Measure Forces F and Moments M

|  | $T_1$ | $T_2$ | $C_1$ | $C_2$ |
|---|---|---|---|---|
| $F_X$ | (A1 + C2) | (B10 + D9) | (A2 + C1) | (B9 + D10) |
| $F_Y$ | (B1 + D2) | (C10 + A9) | (B2 + D1) | (C9 + A10) |
| $F_Z$ | (A3 + A8 + C3 + C8) | (B3 + B8 + D3 + D8) | (A4 + A7 + C4 + C7) | (B4 + B7 + D4 + D7) |
| $M_X$ | (A12 + D14) | (D11 + D13) | (B11 + B13) | (C12 + C14) |
| $M_Y$ | (B12 + B14) | (A11 + A13) | (C11 + C13) | (D12 + D14) |
| $M_Z$ | (A6 + D6) | (B6 + D6) | (A5 + C5) | (B5 + D5) |

Figure 8:
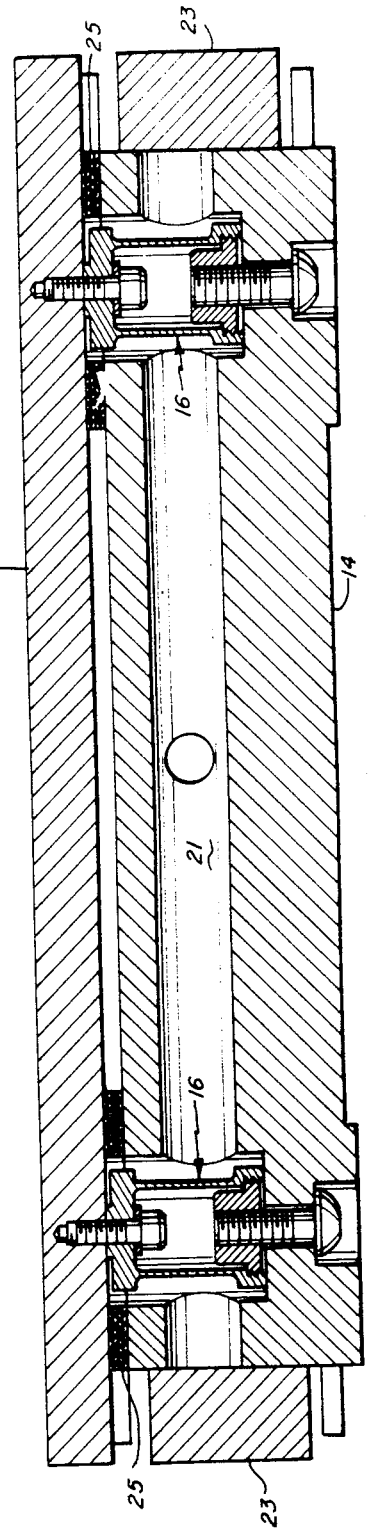
FIG. 8 is an elevational sectional view of a preferred force platform, showing two load cells in cross section.

A preferred platform structure employing the above-described load cells is illustrated in the sectional view of FIG. 8. As in FIG. 1, a top plate 12 is mounted over a bottom plate 14 by load cells 16. The load cells are positioned within a grid-like cavity 21 within the plate 14. That cavity is sealed by end caps 23. Foam rubber pads 25 complete the seal of the inner cavity 21 without providing any vertical support to the top plate 12. The load cell is shown in greater detail in FIG. 9.

Figure 9:
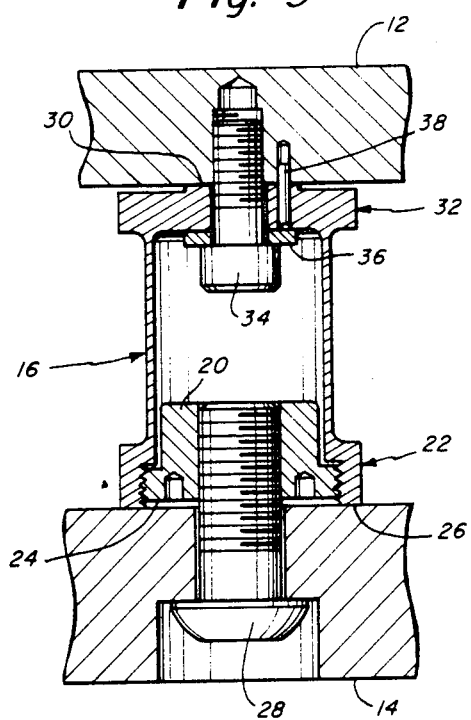
FIG. 9 is an enlarged cross sectional view of a single load cell from FIG. 8.

Each load cell, shown enlarged in FIG. 9, comprises a plug 20 threaded into a cylinder 22. The bottom surface 24 of the plug 20 is set in from the outer rim 26 of the cylinder 22 in order that all forces through the load cell are applied to that outer rim. The load cell is mounted to the bottom plate 14 by a bolt 28 threaded to the plug 20. The centrally applied tensile force of the bolt holds the rim in compression against the bottom plate 14.

A raised surface 30 on the upper, rigid end section 32 provides a support for top plate 12. The top plate is secured to the end section 32 by a bolt 34 secured before assembly of the plug 20 and bottom plate 14.

A washer 36 is positioned between the head of the bolt 34 and the end piece 32. A dowel 38 prevents rotation of the load cell relative to the top plate 12.

As a general rule, strains produced from bending moments are higher than strains due to shear in elastic members. Because of this, multi-component strain gage dynamometers have traditionally utilized elements such as rings in which bending strains due to applied forces are measured. These strains are mechanically and electrically resolved into independent force components. However, there are restraints on the mounting conditions for these bending elements which makes it necessary to compromize on the size, weight, natural frequency, cross talk, and overload ratings for a "satisfactory" multi-component dynamometer.

In order to improve the overall performance of a multi-component dynamometer, load cells have been developed in which either strains due to shear forces or strains due to compressive loading are measured. Inherent in a thin-walled cylinder is a shear strain "magnification" effect, which makes the measured shear strain at the neutral axis twice the average shear strain based upon area. For a given material, a dynamometer with the new load cells has the same vertical sensitivity as one described in our prior U.S. Pat. No. 4,398,429 but the horizontal sensitivity is 2.5 times higher. The lateral stiffness and natural frequency are also much higher, the maximum load capability is increased, and cross talk is minimal even with a relatively flexible top and bottom base.

This invention circumvents an important limitation of previous designs in which bending of the top plate introduced cross talk due to the imposition of bending moments on the strain rings. A previous invention sought to reduce cross talk due to bending of the top plate by introducing flexible ligaments between the top plate and the strain ring which limited the bending moment transmitted to the strain ring. Because the shear strain elements are not sensitive to applied bending moments, they are not sensitive to bending of the top plate, and the need for a rotationallycompliant connection between the top plate and the strain element is eliminated.

The localized contact area for bolting to the top of the load cell ensures an elastic joint between the ring and the top plate. It is only necessary that the ends of the ring be rigid with respect to the thin ring in order that forces are uniformly applied to the ring. The mounting technique used on the bottom of the ring could be used on the top as well.

Stacked rosettes are used for the measurement of $F_X$, $F_Y$, $F_Z$, and $M_Z$ and provide a high degree of thermal compensation for the Wheatstone bridges. The load cells themselves are typically aluminum and are easy to manufacture and gage because of their cylindrical design. Additionally, the simplicity of assembly and an uncomplicated design makes a multi-component dynamometer with the described cylindrical load cells a superior instrument to those previously manufactured.

While the invention has been shown and described with reference to a preferred embodiment thereof, it will be understood by those skilled in the art that various changes in form and detail may be made therein without departing from the spirit and scope of the invention as defined by the appended claims.

We claim:

1. A force measuring apparatus comprising a plate supported on a plurality of load cells, each load cell comprising a cylindrical tubular column having a center axis perpendicular to the plate and having strain gages mounted thereon connected to measure the tensile or compressive strain occurring at 45° to the axis of the load cell and associated with the strain due to forces or moments acting on the load cell parallel to the plate, the strain gauges of a plurality of load cells being interconnected to provide an indication of said forces or moments.

2. A force measuring apparatus comprising a plate supported on a plurality of load cells, each load cell comprising a cylindrical tubular column having a center axis perpendicular to the plate and having strain gages mounted thereon to measure tensile and compressive strain occurring at 45° to the axis of the load cell and associated with the shear strain due to force applied transverse to the center axis of the load cell, the strain gages of a plurality of load cells being interconnected to provide an indication of said force.

3. A force measuring apparatus as claimed in claim 2 further comprising vertical-force-measuring strain gages positioned on opposite sides of each tubular column to measure vertical compression and tension of the load cells and connected in appropriate arms of a Wheatstone bridge to measure vertical force while cancelling out effects of the strain resulting from bending about a horizontal axis.

4. A force measuring apparatus as claimed in claim 2 wherein strain gages mounted on distinct load cells are joined in a bridge circuit to measure moment about an axis parallel to the center axes of the load cells.

5. A force measuring apparatus as claimed in claim 2 further comprising moment measuring vertical compression gages mounted on the tubular columns of respective load cells and joined in a bridge circuit to measure moments about each of two horizontal axes.

6. A force measuring apparatus as claimed in claim 2 wherein each load cell comprises a plug within the tubular column by which the cell is mounted to a base plate, the plug is inset relative to the end surfaces of the tubular column and the tubular column is held against the base plate by a central element in tension between the plug and base plate such that the rim of the tubular column is held in compression by a centrally applied tensile force.

7. A force measuring apparatus as claimed in claim 2 wherein the strain gages are interconnected in a Wheatstone bridge.

8. A force measuring apparatus as claimed in claim 7 wherein at least one pair of the strain gages from each of at least four load cells is connected in a single Wheatstone bridge.

* * * * *